United States Patent [19]

Fan et al.

[11] Patent Number: 5,767,150
[45] Date of Patent: Jun. 16, 1998

[54] CYCLOALIPHATIC EPOXIDE COMPOUNDS

[75] Inventors: Mingxin Fan, West Chester; Gary W. Ceska, Exton; James Horgan, West Chester, all of Pa.; Henri Strub, Pont Sante Maxence, France

[73] Assignee: Sartomer Company, Exton, Pa.

[21] Appl. No.: 831,677

[22] Filed: Apr. 10, 1997

[51] Int. Cl.[6] .................... A61K 31/335; C07D 303/00
[52] U.S. Cl. ............................. 514/475; 549/547
[58] Field of Search ......................... 549/547; 514/475

[56] References Cited

U.S. PATENT DOCUMENTS

| | | | |
|---|---|---|---|
| 2,745,847 | 5/1956 | Phillips et al. | 549/547 |
| 2,750,395 | 6/1956 | Phillips et al. | 549/547 |
| 2,848,426 | 8/1958 | Newey | 528/297 |
| 2,853,498 | 9/1958 | Phillips et al. | 549/547 |
| 2,853,499 | 9/1958 | Phillips et al. | 549/547 |
| 2,857,402 | 10/1958 | Phillips et al. | 549/547 |
| 2,863,881 | 12/1958 | Phillips et al. | 549/547 |
| 2,890,209 | 6/1959 | Phillips et al. | 528/361 |
| 2,917,491 | 12/1959 | Phillips et al. | 528/361 |
| 2,988,554 | 6/1961 | Batzer et al. | 549/547 |
| 3,023,174 | 2/1962 | Batzer et al. | 528/297 |
| 3,057,880 | 10/1962 | Lynn et al. | 549/547 |
| 3,264,230 | 8/1966 | Proops | 528/297 |
| 3,360,501 | 12/1967 | Widmer et al. | 528/271 |
| 3,558,665 | 1/1971 | Friedman et al. | 549/547 |
| 3,671,592 | 6/1972 | Yoshihara et al. | 528/365 |

FOREIGN PATENT DOCUMENTS

| | | |
|---|---|---|
| 392473 | 3/1964 | Japan . |
| 907149 | 10/1962 | United Kingdom . |

OTHER PUBLICATIONS

J. Poly. Sci. Part C: Poly. Lett. 1990, 28,285.
J. Poly. Sci.: Part A: Poly Chem. 1991, 29,547.

*Primary Examiner*—Zinna Northington Davis
*Attorney, Agent, or Firm*—Michael B. Fein; Schnader Harrison Segal & Lewis LLP

[57] ABSTRACT

Compounds having the formula

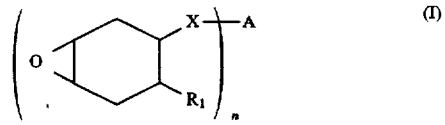

(I)

wherein X is selected from O, $(CH_2)_m O$, S, $(CH_2)_m S$, NH, $(CH_2)_m NH$, $COO^-$, $(CH_2)_m COO^-$, $^-OOC$ and $^-OOC(CH_2)_m$;

m is 1 to 6;

n is 1 to 100;

$R_1$ is $(C_1-C_{20})$ ester; and

A is a saturated organic linking group selected from residues of polyol, polythiol, polyamine, and polyacid, are prepared by reacting compounds according to formula II

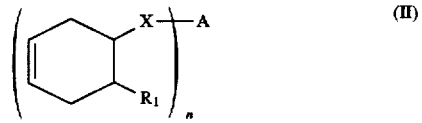

(II)

with hydrogen peroxide in the presence of (a) tungstic acid or its metal salts, (b) phosphoric acid or its metal salts, and (c) at least one phase transfer catalyst.

10 Claims, No Drawings

CYCLOALIPHATIC EPOXIDE COMPOUNDS

BACKGROUND OF THE INVENTION

1. Field of the Invention

This invention relates to cycloaliphatic epoxides and an epoxidation process using hydrogen peroxide as oxidizing agent.

2. Description of the Prior Art

Recently, a variety of unsaturated polymers have been epoxidized with hydrogen peroxide in the presence of a quaternary ammonium tetrakis (diperoxotungsto) phosphate catalyst. (J. Poly. Sci. Part C: Poly. Lett. 1990, 28, 285; J. Poly Sci.: Part A; Poly Chem. 1991, 29, 547). This process suffers from certain disadvantages, e.g., the catalyst is not readily available.

Cyclic epoxides are very reactive towards ring opening reactions due to the high ring strain associated with the ring structure, and thus they are very difficult to prepare. Cyclic epoxide precursors are very sensitive to reaction conditions. Currently, these precursors are epoxidized using peracids with careful pH control. Organic acids are used and generated during the epoxidation process.

Cyclic olefins have been epoxidized under phase transfer conditions. However, unsaturated cyclic substrates containing ester or ether linkages are sensitive to side reactions such as cleavage. Epoxidation of these types of substrates under phase transfer conditions has not been demonstrated in the prior art.

U.S. Pat. Nos. 3,360,501; 3,023,174; and 2,988,554; and UK specification 907,149, assigned to Ciba Ltd.; and U.S. Pat. Nos. 2,917,491; 2,890,209; 2,863,881; 2,853,499; 2,853,498; 2,745,847; and 2,750,395 assigned to Union Carbide Corporation teach processes which can produce cyclic epoxides having up to two cycloaliphatic rings. U.S. Pat. Nos. 3,671,592 assigned to Nitto Electric Industrial Co.; and 3,558,665 assigned to Argus Chemical Co., and Japanese Kokai 39-2473 of Mar. 10, 1964 assigned to Kanegafuchi Spinning Co., Ltd., also teach processes which can produce cyclic epoxides having only up to two cycloaliphatic rings.

Processes for producing cyclic epoxides having three or more cycloaliphatic rings have not been provided or suggested by the prior art.

SUMMARY OF THE INVENTION

It is an object of the present invention to eliminate the use of organic acids in the process of epoxidation of cyclic, aliphatic, unsaturated compounds.

It is a further object of the invention to simplify the epoxidation process and use hydrogen peroxide directly as epoxidation agent.

A still further object is to provide a new class of cycloaliphatic epoxides having at least three cycloaliphatic rings.

These objects, and others which will become apparent from the following disclosure, are achieved by the present invention which comprises in one aspect a process of preparation of compounds of formula I

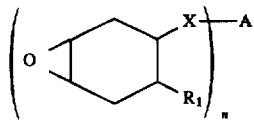

wherein
X is selected from O, $(CH_2)_mO$, S, $(CH_2)_m$ S, NH, $(CH_2)_m NH$, $COO^-$, $(CH_2)_m COO^-$, $^-OOC$ and $^-OOC(CH_2)_m$;
m is 1 to 6;
n is 1 to 100;
$R_1$ is $(C_1-C_{20})$ ester; and
A is a saturated organic group selected from residues of alcohol, polyol, thiol, polythiol, amine, polyamine, acid, and polyacid; comprising reacting a compound of formula II

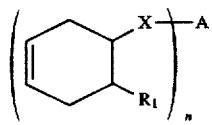

with hydrogen peroxide in the presence of (a) tungstic acid or its metal salts, (b) phosphoric acid or its metal salts, and (c) at least one phase transfer catalyst.

In another aspect, the invention comprises compounds of formula I, wherein n is 3 to 100.

The invention also comprises compositions comprising a polymer prepared by curing a compound of formula I wherein n is 3 to 100 in the presence of a cationic initiator.

DETAILED DESCRIPTION OF THE INVENTION AND PREFERRED EMBODIMENTS

The new method involves low level of catalyst composition and no organic acid and/or peracid, which results in simple product workup and process. The present invention uses hydrogen peroxide in the presence of (a) tungstic acid or its metal salts, (b) phosphoric acid or its metal salts, (c) at least one phase transfer catalyst. The epoxidation of unsaturated cyclic substrates with hydrogen peroxide in the presence of tungsten catalyst, phosphoric acid or its salt, and phase transfer catalyst can be performed at any temperature which is sufficient to react, however, particularly suitable temperatures are between 0° C. and 100° C., preferably from 25° C. to 70° C. The reaction takes place faster at higher temperature and requires shorter time to complete. The reaction is typically exothermic. Slow addition of hydrogen peroxide is preferred to control the exotherm. The reaction can be performed at pressures from subatmospheric to superatmospheric; however, the reaction is preferably carried out at atmospheric pressure.

The epoxidation can be performed with or without solvent. Solvent can be used to reduce the viscosity. If solvent is needed, water immiscible organic solvents such as chlorinated hydrocarbons, ethers, glycol ethers, hydrocarbons, combinations thereof, can be used. Particular suitable organic solvents are toluene, chlorobenzene, chloroform, methylene chloride, and the like.

Hydrogen peroxide solution is used as oxidant in the concentration of 5 to 70%. The amount of hydrogen peroxide can vary depending on the desired degree of epoxidation, typically from 0.1 to 1.5 equivalent per unsaturated double bond.

The phase transfer catalyst can be used from 0.001 to 1, preferably 0.05 to 0.1, equivalents per equivalent of carbon-carbon double bond. Suitable phase transfer catalysts includes quaternary ammonium salts, quaternary phosphonium salts, and polyethers; for example, trioctylmethyl ammonium chloride, trioctylmethyl ammonium bromide, trioctylmethyl ammonium iodide, trioctylmethyl ammonium hydrogen sulfate, trioctylmethyl ammonium nitrate, tetrahexyl ammonium chloride, tetrahexyl ammonium bromide, tetrahexyl ammonium iodide, tetrahexyl ammonium hydrogen sulfate, tetrahexyl ammonium nitrate, tetrabutyl ammonium chloride, tetrabutyl ammonium bromide, tetrabutyl ammonium nitrate, tetrabutyl ammonium hydrogen sulfate, dioctadecyldimethyl ammonium chloride, dioctadecyldimethyl ammonium bromide, dioctadecyldimethyl ammonium nitrate, dioctadecyldimethyl ammonium hydrogen sulfate, dihexadecyldimethyl ammonium chloride, dihexadecyldimethyl ammonium bromide, dihexadecyldimethyl ammonium nitrate, dihexadecyldimethyl ammonium hydrogen sulfate, trioctylmethylphosphonium chloride, trioctylmethylphosphonium bromide, trioctylmethylphosphonium nitrate, trioctylmethylphosphonium hydrogen sulfate, tetrahexylphosphonium chloride, tetrahexylphosphonium bromide, tetrahexylphosphonium nitrate, tetrahexylphosphonium hydrogen sulfate, tetrabutylphosphonium chloride, tetrabutylphosphonium bromide, tetrabutylphosphonium nitrate, tetrabutylphosphonium hydrogen sulfate, tetrabutylphosphonium iodide, dioctadecyldimethylphosphonium chloride, dioctadecyldimethylphosphonium bromide, dioctadecyldimethylphosphonium nitrate, dioctadecyldimethylphosphonium hydrogen sulfate, dihexadecyldimethylphosphonium chloride, dihexadecyldimethylphosphonium bromide, dihexadecyldimethylphosphonium nitrate, dihexadecyldimethylphosphonium hydrogen sulfate, tetraalkyl ammonium hydroxide, tetraalkyl ammonium tribromide, tetraalkyl ammonium trifluoromethanesulfonate, polyethyleneglycol, polypropyleneglycol, polyethylene glycol-polypropylene glycol copolymer, any combination thereof and the like.

Phosphoric acid or its various salts can be used from 0.001 to 0.5 equivalents per equivalent of carbon-carbon double bond. Sodium or potassium salts of monobasic, dibasic, or tribasic salts of phosphoric acid can also be used. The final pH can be adjusted by other acids or bases to 0–5.

Tungsten catalysts can be used from 0.001 to 50% by weight based on the cyclic substrates. Tungstic acid or its metal salts can be used as the metal catalysts, the metal salts are water soluble and the acid is not. The typical catalyst is used from 0.005 to 1% and the preferred catalyst is tungstic acid which is not water soluble. Molybdenum derivatives may be used instead of tungsten compounds. Either tungstic acid which is not water soluble or its metal salts which are soluble can be used as the metal catalyst. The typical catalyst is used in amounts of about 0.005 to 1%, based on weight of unsaturated compound. The preferred metal catalyst is tungstic acid.

The expoxidation can be performed with or without solvent. The use of solvent is preferred because it reduces the viscosity. If solvent is desired, a water immiscible organic solvent such as chlorinated hydrocarbons, and ethers, glycol ethers, hydrocarbons, and combinations thereof, are especially useful. Particularly suitable organic solvents are toluene, chlorobenzene, chloroform, methylene chloride, heptane, and the like.

The method of the invention allows use of a low level of catalyst composition free of organic acid and/or peracid, resulting in simple product workup and process, and using readily available catalysts.

The new class of cyclic epoxides have the general formula:

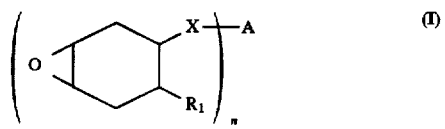

wherein
O, $(CH_2)_mO$, S, $(CH_2)_m$ S, NH, $(CH_2)_m NH$, COO$^-$, $(CH_2)_m$ COO$^-$, $^-$OOC and $^-$OOC $(CH_2)_m$;
m is 1 to 6;
n is 3 to 100;
$R_1$ is $(C_1-C_{20})$ ester; and
A is a saturated organic linking group selected from residues of polyol, polythiol, polyamine, and polyacid.

Suitable organic linking groups A in the case of the process are selected from alcohols, polyols, thiols, polythiols, amines, polyamines, acids, and polyacids. Suitable alcohols include methanol, ethanol, propanol, and the like, up to $C_{18}$ alcohols. Suitable polyols include, for example, 1,4-butane diol, 1,6-hexane diol, trimethylopropane, pentocrithritol, polyvinyl alcohol, dipentarithritol. Suitable acids include, for example, acrylic and methacrylic acid, whereas suitable polyacids include, for example, succinic acid, adipic acid, polyacrylic acid and copolymers thereof. Examples of amines include monoethanol amine, butylamine, diethyl amine, diethanolamine, and the like. Examples of thiols are the thiol analogues of the alcohols and polyols.

In the case of the compounds, where n is 3 to 100, suitable organic linking groups, A, are residues from residues of polyols, polythiols, polyamines, and polyacids having a functionality of 3 to 100.

Suitable $(C_1-C_{20})$ alkyl groups are methyl, ethyl, propyl, butyl, and the like, with butyl preferred.

Suitable $(C_1-C_{20})$ alkoxy groups are methoxy, ethoxy, and the like, and alkoxylated alkoxy groups.

Suitable $(C_1-C_{20})$ ester groups are alkyl ester groups such as methyl esters, and the like.

X is selected from O, $(CH_2)_mO$, S, $(CH_2)_m$ S, NH, $(CH_2)_m NH$, COO$^-$, $(CH_2)_m$ COO$^-$, $^-$OOC and $^-$OOC $(CH_2)_m$; wherein m is 1 to 6. The most preferred X groups are O, COO$^-$; and $^-$OOC. In the product of the process of the invention defined by formula I, whenever n is 2 or more each X can be different, but is preferably the same.

Diepoxides, wherein n is 2, are preferred in the case of the process.

The novel cyclic epoxides produced by the process of the invention can be used in applications such as coatings, epoxy/amine cure, cationic cure, and chemical intermediates for functionalizations.

EXAMPLES

The following non-limiting examples are presented to illustrate a few embodiments of the invention. All parts and percentages are by weight unless otherwise indicated.

Example 1

Preparation of Ethylenically Unsaturated Diester

Tetrahydrophthalic anhydride (152.2 g), 1-butanol (74.1 g) were added to the reactor and the mixture was heated while stirring to 110° C. Exothermic reaction took place and the reactor temperature reached to 150° C. Water cooling was applied to control the temperature at 110° C. The reaction was kept at 110° C. for two hours when the acid anhydride absorption disappeared based on FTIR. Tetrahydrophthalic anhydride butyl half ester was obtained.

After cooling, 1,4-butanediol (46.0 g), toluene (60.0 g), heptane (60.0 g), and methane sulfonic acid (70%, 8.0 g) were added, the mixture was stirred and heated to reflux. Esterification took place and the water formed was removed azeotropically; esterification was completed in three hours and 20.2 grams of water was collected. The reaction mixture, after cooling down to room temperature, was washed with 25.0 g of 25% sodium hydroxide twice. The final product was isolated by removing the solvents under reduced pressure (yield 205.0 g).

Example 2

Preparation of Diepoxide from Unsaturated Diester

Product from Example 1(100.0g) was added to a reactor, followed by tungstic acid (0.80 g), phosphoric acid (85%, 0.40 g), sodium hydroxide (25%, 0.40 g), Aliquot 336 (0.80 g), and toluene (200.0 g). The mixture was stirred and heated to 50° C. when slow addition of hydrogen peroxide (30%, 65.0 ml) began. The hydrogen peroxide addition was completed in 70 minutes to control the exotherm. The reaction mixture was kept at 50° C. for 2.5 additional hours when no residual starting material was detected by GC and FTIR.

The final mixture was separated into two phases. The organic phase was isolated and washed twice with 50 ml of water to remove the excess hydrogen peroxide. The final dicycloaliphatic epoxide was isolated by removing solvent at 95° C. under reduced pressure which has epoxy equivalent weight of 280.1 g/eq (yield 94.0 g).

Example 3

Preparation of Unsaturated Dicyclic Diester

6-Methyl-3-cyclohexene-1-1-methanol (180.0 g), adipic acid (100.0 g), heptane (120.0 g), and methanesulfonic acid (70%, 6.0 g) were added to a reactor which was equipped with a mechanical stirrer, condenser, thermal couple. The reaction mixture was heated to reflux under stirring and esterification process took place. The water formed was removed azeotropically while refluxing. The reaction was completed in 6 hours and the final temperature was 110° C.; 26.6 grams of water was collected.

The final reaction mixture was washed with 10.0 g of 25% sodium hydroxide after cooling down to room temperature. The final dicyclic diester was isolated by removing the heptane solvent at 95° C. under reduced pressure (yield 237.0 g).

Example 4

Preparation of Diepoxide from Unsaturated Dicyclic Diester

Unsaturated dicyclic diester from Example 3 (100.0 g) was added to a reactor, followed by tungstic acid (0.80 g), phosphoric acid (85%, 0.40 g), sodium hydroxide (25%, 0.40 g), Aliquot 336 (0.80 g), and toluene (200.0 g). The mixture was stirred and heated to 50° C. when slow addition of hydrogen peroxide (30%, 70.0 ml) began. The hydrogen peroxide addition was completed in 40 min to control the exotherm. The reaction mixture was kept at 50° C. for 2.0 additional hours when no residual starting material was detected by GC and FTIR.

The final mixture was separated into two phases, the organic phase was isolated and washed twice with 50 ml of water to remove the excess hydrogen peroxide. The final dicycloaliphatic epoxide was isolated by removing solvent at 95° C. under reduced pressure which has epoxy equivalent weight of 207.0 g/eq (yield 105.0 g).

Example 5

Preparation of Esters

Tetrahydrophthalic anhydride (152.2 g), and 1-butanol (74.1 g) were added to the reactor, the mixture was heated while stirring to 110° C. Exothermic reaction took place and the reactor temperature reached to 150° C., and then water cooling was applied and the temperature was controlled at 110° C. The reaction was kept at 110° C. for two hours when the acid anhydride absorption disappeared based on FTIR.

After cooling, trimethylolpropane (44.7 g), heptane (110.0 g), and methane sulfonic acid (70%, 8.0 g) were added. The mixture was then stirred and heated to reflux. Esterification took place and the water formed was removed azotropically. Esterification completed in three hours and 19.43 grams of water was collected. The reaction mixture, after cooling down to room temperature, was washed with 25.0 g of 25% sodium hydroxide twice. The final product was isolated by removing the solvents under reduced pressure (yield 235.0 g).

Example 6

Preparation of triepoxides

The product from Example 5 (172.0 g) was added to a reactor, followed by tungstic acid (1.43 g), phosphoric acid (85%, 0.70 g), sodium hydroxide (25%, 0.70 g), Aliquat 336 (1.41 g), and toluene (300.0 g). The mixture was stirred and heated to 60° C. when slow addition of hydrogen peroxide (30%, 100.0 ml) was begun. The hydrogen peroxide addition was completed in 70 min to control the exotherm. The reaction mixture was kept at 60° C. for 12.0 additional hours after which no residual starting material was detected by GC and FTIR. The final mixture was separated into two phases. The organic phase was isolated and washed twice with 50 ml of water to remove the excess hydrogen peroxide. The final tricycloaliphatic epoxide product was isolated by removing solvent at 70° C. under reduced pressure. The product had an epoxy equivalent weight of 350.0 g/eq (yield 146.3 g).

While the invention has been described in sufficient detail for those skilled in the art to make and use it, various modifications, alternatives, and improvements should become readily apparent without departing from the spirit and scope of the invention as set forth in the following claims.

What is claimed is:

1. A compound of the formula

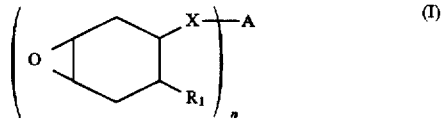

wherein

X is selected from O, $(CH_2)_m O$, S, $(CH_2)_m$ S, NH, $(CH_2)_m NH$, $COO^-$, $(CH_2)_m COO^-$, $^-OOC$ and $^-OOC(CH_2)_m$;

m is 1 to 6;

n is 3 to 100;

$R_1$ is $(C_1-C_{20})$ ester; and

A is a saturated organic linking group selected from residues of polyol, polythiol, polyamine, and polyacid.

2. A compound according to claim 1 wherein $R_1$ is an ester group of the formula —$COOR_2$ wherein $R_2$ is selected from the group consisting of ($C_1$–$C_{20}$) alkyl.

3. A compound according to claim 1 wherein A is selected from residues of ($C_1$–$C_{20}$) alkylene triols, tri-thiols, triamines, and triacids.

4. A compound according to claim 1 wherein n is 3 to 5.

5. A compound according to claim 1 wherein n is 3.

6. A compound according to claim 1 wherein m is 1.

7. A compound according to claim 3 wherein n is 3, m is 1, and X is $COO^-$ or $^-OOC$.

8. A compound according to claim 1 wherein A has 1 to 36 carbon atoms.

9. A compound according to claim 1 wherein X is $COO^-$, n is 3, $R^1$ is is an ester group of the formula —$COOR_2$ wherein $R_2$ is butyl, and A is the residue of trimethylolpropane.

10. A composition comprising a polymer prepared by curing a compound according to claim 1 in the presence of a cationic initiator.

* * * * *